United States Patent [19]
Burnett et al.

[11] Patent Number: 5,747,064
[45] Date of Patent: May 5, 1998

[54] PSORIASIS TREATMENT

[75] Inventors: Debbie L. Burnett, Basking Ridge; Darius D. Dubash, Pine Brook; Athanasios S. Ladas, Parsippany; Victor M. Wong, Hackettstown, all of N.J.

[73] Assignee: Pfizer Inc., New York, N.Y.

[21] Appl. No.: 895,719

[22] Filed: Jul. 17, 1997

Related U.S. Application Data

[60] Continuation of Ser. No. 444,180, May 18, 1995, abandoned, which is a division of Ser. No. 98,497, Jul. 28, 1993, abandoned.

[51] Int. Cl.$^6$ .................. A61L 25/00; A61L 15/24; A61K 9/70
[52] U.S. Cl. .................. 424/443; 424/45; 424/78.31; 424/78.05; 602/52; 514/863
[58] Field of Search .................. 514/772.6, 863; 424/78.31, 78.05, 443, 45; 602/41–43, 52

[56] References Cited

U.S. PATENT DOCUMENTS

| | | | |
|---|---|---|---|
| 4,210,633 | 7/1980 | Tarhuri | 424/80 |
| 4,575,515 | 3/1986 | Sandborn | 514/708 |
| 4,652,557 | 3/1987 | Sandborn | 514/164 |
| 4,826,677 | 5/1989 | Mueller et al. | 424/78 |

FOREIGN PATENT DOCUMENTS

| | | |
|---|---|---|
| 9102538 | 3/1991 | WIPO . |
| 9204019 | 3/1992 | WIPO . |

*Primary Examiner*—Edward J. Webman
*Attorney, Agent, or Firm*—Peter C. Richardson; Paul H. Ginsburg; Grover F. Fuller, Jr.

[57] ABSTRACT

The present invention is directed to a topical composition for the treatment of psoriasis. The composition comprises a film forming agent, especially vinyl acetate crotonic acid copolymer a plasticizer, an aqueous alcoholic solution and an amount of alkali effective to prevent the gellation of the film forming agent.

1 Claim, No Drawings

PSORIASIS TREATMENT

This is a continuation of application Ser. No. 08/444,180, abandoned filed on May 18, 1995, which, in turn, is a division of application Ser. No. 08/098,497 filed on Jul. 28, 1993 abandoned.

BACKGROUND OF THE INVENTION

The present invention is directed to a topical composition for the treatment of psoriasis.

Psoriasis is a skin disease marked by the presence of small elevations of the skin as well as silvery scales. In the area where scales have been shed, tiny bleeding points called "Auspitz sign" appear. The major pathophysiological events involved in the disease process are accelerated epidermal proliferation and metabolic activity, proliferation of capillaries in the dermal region, and invasion of the dermis and epidermis by inflammatory cells.

Coal Tar and Salicylic Acid are the only two Category I drugs mentioned in the Final Monograph for dandruff, seborrheic and psoriatic drugs. There are a number of prescription products (different drug entities) that are also useful, e.g. Theophylline which arrests the proliferation of cells during the metaphase stage of cell division.

It is also known that psoriatic zones lose water 8–10 times faster than normal skin. This leads to increased metabolic rates at the expense of tissue catabolism and muscle wasting.

U.S. Pat. No. 4,210,633 issued Jul. 1, 1980 refers to treatment of psoriasis by application of a film forming composition containing flurandrenolide. The film forming components are polyvinyl alcohol and polyvinylpyrrolidone.

French Patent Number 2539 refers to a psoriasis treatment comprising a thin plastic film, for example, vinyl polymers, polyamides or polyesters, impregnated with a corticoid.

Australian Patent Number 6218907 refers to a pharmaceutical composition for the treatment of psoriasis comprising coal tar and a flexible carrier material.

West German Offenleguschrift Number 297329 refers to a pharmaceutical composition for the treatment of localized psoriasis which comprises a copolymer of acrylic acid esters and/or methacrylic acid esters as the active agent. The composition is applied as a fine spray which forms an elastic film.

PCT Application Number 92/04019 refers to the use of 6-methoxy-2-naphthylacetic acid as a topical treatment for psoriasis.

PCT Application Number 91/02538 refers to a composition for treating keratinous tissue, e.g. psoriasis, in mammals comprising a film forming protein, a compatible reducing agent, a reactive zinc salt and at least one film-forming polymer.

U.S. Pat. No. 4,826,677 issued May 2, 1989 refers to a liquid formulation for the treatment of psoriasis containing dithranol dispersed in a film forming polymer.

European Patent Application Number 223671 refers to an antipsoriatic composition containing a corticosteroid and a beta-agonist. The composition may be applied as a film.

U.S. Pat. No. 4,652,557 issued Mar. 24, 1987 and U.S. Pat. No. 4,575,515 issued Mar. 11, 1986 refer to a topical solution for psoriasis treatment. The solution contains dimethyl sulfoxide, a polyalcohol, a dispersant, triethanolamine salicylate and water.

United Kingdom Patent Number 2165453 refers to a topical composition for the treatment of psoriasis which comprises dithranol distributed in the adhesive layer of a non-permeable self-adhesive film.

Japanese Patent Number 56061312 refers to an adhesive sheet for curing skin diseases which contains betamethazone valerate in the adhesive base.

SUMMARY OF THE INVENTION

In one embodiment, the present invention is directed to a composition comprising:

(a) a film-forming agent, (b) a plasticizer, (c) an aqueous alcoholic solution, (d) an amount of alkali effective to prevent the gellation of said film-forming agent, said composition, when applied to a psoriatic zone of the skin of a human, forming an occlusive area suppressing greater than 70 percent of water transmission from the psoriatic zone.

Preferred is the composition wherein said film-forming agent is vinyl acetate crotonic acid copolymer.

Also preferred is the composition wherein said plasticizer is dibutyl sebacate.

In a preferred embodiment, the present invention is directed to a composition comprising:

(a) from about 50 to about 90 weight percent alcohol in an aqueous solution, (b) from about 0.01 to about 0.5 weight percent alkali, (c) from about 5 to about 25 weight percent film-forming agent, and (d) from about 0.01 to about 0.2 weight percent plasticizer, said composition, when applied to a psoriatic zone of the skin of a human, forming an occlusive area suppressing greater than 70 percent of water transmission from the psoriatic zone.

Preferred is the composition wherein said alkali is potassium hydroxide.

Also preferred is the composition wherein said film-forming agent is vinyl acetate crotonic acid copolymer.

Especially preferred is the composition wherein said plasticizer is dibutyl sebacate.

In another embodiment, the present invention is directed to a method for the treatment of psoriasis in a human in need of such treatment comprising the application to the psoriatic zone of a composition of the present invention.

DETAILED DESCRIPTION OF THE INVENTION

The present invention is directed to a spray-on patch for psoriasis. The solution which forms the patch is formulated so that when sprayed onto the psoriatic zone by, for example, a pump spray, it sets in a short period of time and forms a flexible skin, thereby preventing water transmission from the psoriatic zone.

One component of the formulation is a film-forming agent. An especially preferred film-forming agent is vinylacetate crotonic acid copolymer. When used in the formulation, it is present at a concentration of from about 5 to about 25 weight percent, preferably at about 13 weight percent.

Another component of the formulation is a plasticizer. An especially preferred plasticizer is dibutyl sebacate. When used in the formulation, dibutyl sebacate is present at a concentration of from about 0.01 to about 0.2 weight percent, preferably at about 0.05 weight percent.

Since the film-forming agent of the present formulation has a tendency towards gellation, the present formulation also contains a small amount of alkali to prevent gelling thus promoting the occlusive properties of the patch. A preferred alkali is potassium hydroxide. The alkali is present at a concentration of from about 0.01 to about 0.5 weight percent, preferably at about 0.20 weight percent.

Another component of the formulation of the present invention is an aqueous alcoholic solution. It has been found that if less than 200 proof (100%) alcohol is used, the small amount of water present adds to the occlusive properties of the spray or patch. In the formulation of the present invention, the aqueous alcoholic solution is present at a concentration of from about 50 to about 90 weight percent, preferably at about 87 weight percent. Alternatively, a 200 proof alcohol can be diluted to a 180–190 proof (90–95%) alcohol by the addition of water. Such diluted aqueous alcoholic solutions can also be used in the formulations of the present invention.

The formulation of the present invention may be packaged in any container. A preferred package is one containing a suitable spraying device. A simple pump spray may be used. A moderate pressure aerosolized spraying device may also be used. The formulation may also be packaged in a container with a brush or sponge-type applicator or a roll-on container.

Having described the invention in general terms, reference is now made to specific examples. It is to be understood that these examples are not meant to limit the invention, the scope of which is determined by the appended claims.

EXAMPLE 1

A formulation was prepared with the following ingredients.

| Ingredient | % w/w |
| --- | --- |
| Alcohol, USP[1] | 86.75 |
| Potassium Hydroxide NF | 0.20 |
| Vinyl Acetate Crotonic Acid Copolymer[2] | 13.00 |
| Dibutyl Sebacate[3] | 0.05 |
| | 100.00 |

[1]190 Proof Ethyl Alcohol
[2]Vinac ® ASB-516
[3]Uniflex ® DBS

The formulation was prepared in the following manner.

Into a 500 ml stainless steel beaker was charged 260.25 grams of alcohol (USP Ethanol 190 proof). The alcohol was mixed with a Lightnin mixer at 500 RPM to generate a vortex.

0.60 grams of potassium hydroxide were added and dissolved by mixing at 500 RPM for three minutes.

39.00 grams of vinylacetate crotonic acid copolymer (Vinac® ASB-516) was then added and the resultant solution was mixed at 500 RPM for one hour. To insure that all the Vinac® had dissolved, mixing was continued for an additional 30 minutes.

After all the Vinac® had dissolved, 0.15 grams of dibutyl sebacate was added and the solution was mixed for five minutes. The final solution was discharged into an 8 ounce clear glass bottle.

The solution had the following physical characteristics.

| | | |
| --- | --- | --- |
| 1. | Drying Time | 3–4 minutes |
| | Sprayability | Satisfactory |
| 2. | pH | 7.33 |
| 3. | Viscosity | 23.07 CPS |
| 4. | Specific Gravity | 0.8505 |

When sprayed onto a psoriatic zone, the solution set into a flexible skin which showed greater than 70% suppression of water transmission.

We claim:

1. A method for the treatment of psoriasis in a human in need of such treatment comprising the application to the psoriatic zone of a composition consisting essentially of:

(a) from about 50 to about 90 weight percent alcohol in an aqueous solution, (b) from about 0.01 to about 0.5 weight percent alkali, (c) from about 5to about 25 weight percent vinyl acetate crotonic acid coplymer, and (d) from about 0.01 to about 0.2 weight percent plasticizer, said composition, when applied to a psoriatic zone of the skin of a human, forming an occlusive area suppressing greater than 70 percent of water transmission from the psoriatic zone.

* * * * *